United States Patent
Butz

(10) Patent No.: US 9,187,218 B2
(45) Date of Patent: Nov. 17, 2015

(54) CLOSURE DEVICE

(71) Applicant: Siemens Healthcare Diagnostics Products GmbH, Marburg (DE)

(72) Inventor: Thomas Butz, Hochheim am Main (DE)

(73) Assignee: SIEMENS HEALTHCARE DIAGNOSTICS PRODUCTS GMBH, Marburg (DE)

(*) Notice: Subject to any disclaimer, the term of this patent is extended or adjusted under 35 U.S.C. 154(b) by 104 days.

(21) Appl. No.: 14/154,715

(22) Filed: Jan. 14, 2014

(65) Prior Publication Data

US 2014/0199208 A1     Jul. 17, 2014

(30) Foreign Application Priority Data

Jan. 15, 2013   (EP) ..................... 13151264

(51) Int. Cl.
*B01L 99/00* (2010.01)
*B65D 43/02* (2006.01)
*B01L 3/00* (2006.01)
*G01N 35/10* (2006.01)
*G01N 35/04* (2006.01)

(52) U.S. Cl.
CPC .............. *B65D 43/02* (2013.01); *B01L 3/523* (2013.01); *G01N 35/1002* (2013.01); *G01N 2035/0405* (2013.01)

(58) Field of Classification Search
CPC ........ B01L 3/523; B65D 43/20; B65D 43/02; G01N 2035/0405
See application file for complete search history.

(56) References Cited

U.S. PATENT DOCUMENTS

| | | | |
|---|---|---|---|
| 5,510,082 | A | 4/1996 | Arai et al. |
| 5,620,898 | A | 4/1997 | Yaremko et al. |
| 2007/0189924 | A1 | 8/2007 | Knight |
| 2008/0063567 | A1 | 3/2008 | Schacher et al. |

FOREIGN PATENT DOCUMENTS

| | | |
|---|---|---|
| EP | 1918721 A1 | 5/2008 |
| JP | 2000131328 | 5/2000 |

OTHER PUBLICATIONS

European Search Report and Written Opinion of European Patent Application No. 13151264.2 dated Aug. 1, 2013.

*Primary Examiner* — Paul Hyun
(74) *Attorney, Agent, or Firm* — Dugan & Dugan, PC

(57) ABSTRACT

A closure device (1) for closing an opening in a container lid and the use of the closure device (1) in a container lid is provided for covering reagent vessel containers in automatic analysis apparatus. The closure device comprises a fastening element (2), a closure element (20), two levers (14), and a plurality of bearings (18, 16, 24).

19 Claims, 6 Drawing Sheets

CLOSURE DEVICE

Figure 1:
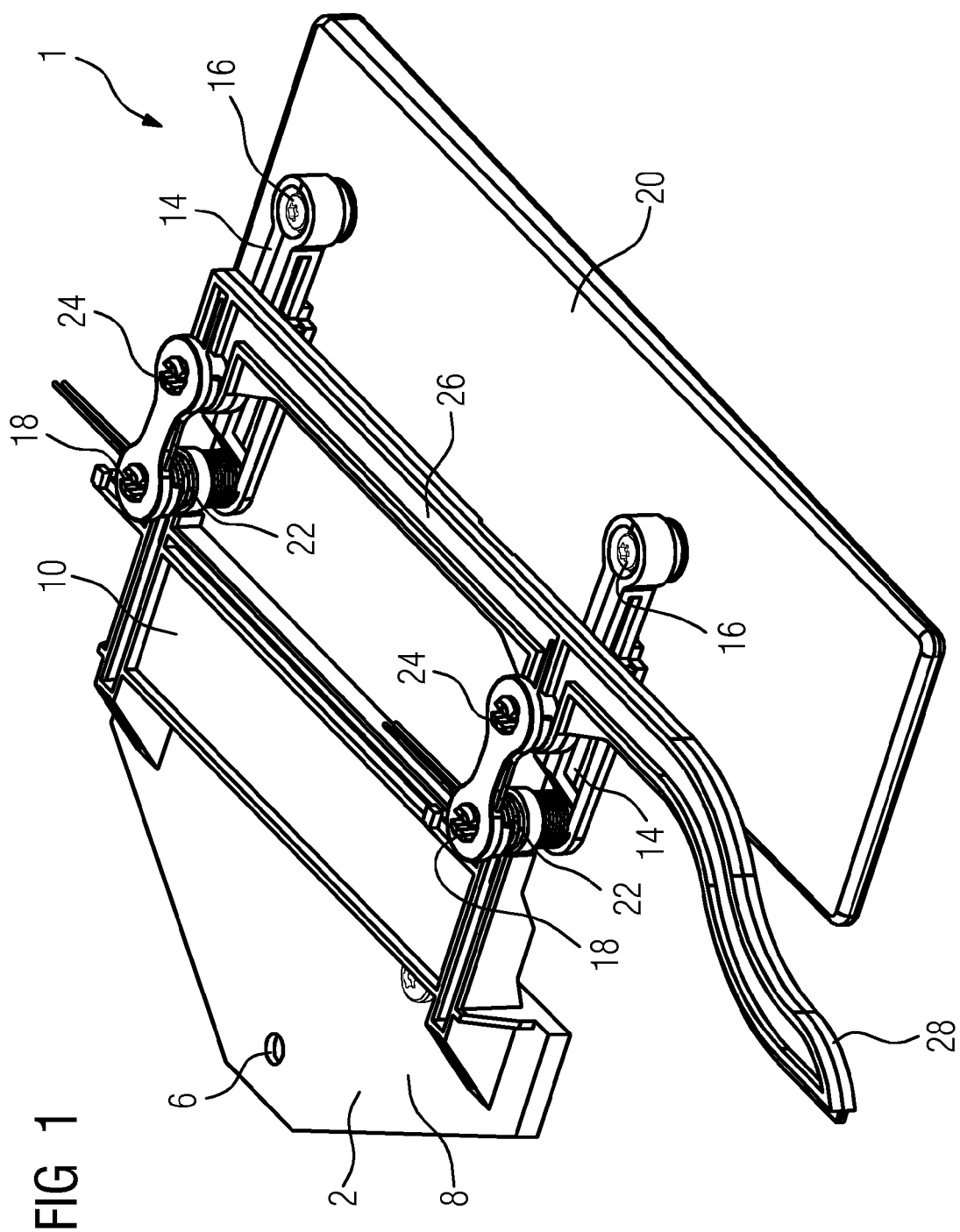

The invention relates to a device for closing an opening in a container lid, and to the use of said device in a container lid that is provided for covering reagent vessel containers in automatic analysis apparatus.

Numerous detection and analysis methods for determining physiological parameters in samples of bodily fluid such as blood, plasma, serum or urine or in other biological samples are carried out in an automated manner in corresponding analysis apparatus.

Current analysis apparatus are able to carry out many different kinds of detection reactions and analyses with a large number of samples. Analysis apparatus of the kind presently used in clinical laboratories or in blood banks usually comprise an area for the delivery of sample vessels that contain the primary samples to be analyzed. To feed the sample vessels into the analysis apparatus, a transport system is usually provided which firstly transports the sample vessels to a sample identification device, which detects sample-specific information applied to a sample vessel and transmits said information to a storage unit. Thereafter, the sample vessels are transported to a sampling station. With the aid of a sample pipetting device, at least one aliquot of the sample liquid is removed there from a sample vessel and is transferred to a reaction vessel.

Measurement systems which are based on photometric (e.g. turbidimetric, nephelometric, fluorometric or luminometric) or radiometric measurement principles are particularly common. These methods permit the qualitative and quantitative detection of analytes in liquid samples, without having to provide additional separating steps. Clinically relevant parameters, such as the concentration or the activity of an analyte, are often determined by virtue of an aliquot of a bodily fluid of a patient being mixed, simultaneously or in succession, with one or more test reagents in the reaction vessel, as a result of which a biochemical reaction is started which brings about a measurable change in an optical property of the test mixture.

The measurement result is in turn forwarded by the measurement system to a storage unit and evaluated. Subsequently, the analysis apparatus supplies sample-specific measurement values to a user via an output medium, e.g. a monitor, a printer or a network connection.

The reagents required for providing different, test-specific reaction mixtures are usually stored in corresponding single-chamber or multi-chamber reagent vessels in a reagent vessel container in a reagent station of the apparatus. In view of the large number of different analyses to be carried out, this reagent vessel container typically has a large number of receiving positions for reagent vessels and, in many cases, it also has a cooling unit in order to ensure the shelf life of the reagents. The analysis apparatus accesses the stock of reagents in an automated manner and, as and when necessary, by means of a transfer arm with a pipetting device, removes the reagents that are needed for the particular analysis.

For the reagents to be cooled without using too much energy, the reagent vessel container is typically carefully insulated and comprises a container lid. However, at least one opening has to be left in the container lid in order to be able to remove the required liquid reagents by means of the pipetting device. Since pipetting devices in the form of hollow needles have a relatively small diameter and can also be moved with very great precision, the openings provided in the container lid for the passage of a pipetting needle can be kept relatively small. The heat exchange that occurs through pipetting holes or pipetting slits in the container lid is therefore largely unproblematic. More problematic is the heat exchange through openings in the container lid that are intended to permit the exchange of reagent vessels. The dimensions of such openings are much greater than those of the pipetting holes, so as to ensure that a reagent vessel can be inserted through the opening into the reagent vessel container or removed therefrom. A reagent vessel container with a container lid, which has a pipetting hole and an opening for the exchange of reagent vessels, is known from EP-A1-1918721.

The object of the present invention was therefore to make available a container lid with openings, which container lid has reduced heat exchange between the interior of the container and the area around the container.

The object is achieved by the fact that a closure device is made available for an opening in the container lid, as a result of which the opening can be opened during an access procedure and can be closed out with an access procedure. The closure device according to the invention permits tight and insulating closure of the opening of the container lid and minimizes the opening time during automatic opening and closure.

The subject matter of the present invention is therefore a device for closing an opening in a container lid. The device comprises a fastening element for fastening the device on the container lid, a closure element, which is connected movably to the fastening element and which, in a closed position, covers the opening of the container lid and, in an open position, does not cover the opening of the container lid. The device further comprises a guide rail, which is connected movably to the fastening element and to the closure element. A horizontal force can act on the guide rail, as a result of which the closure element is movable from the closed position to the open position. The fastening element and the closure element are connected by a pair of mutually parallel levers. Each of the levers is mounted rotatably in a fastening-element-side bearing and in a closure-element-side bearing, wherein the bearings have a rotation axis perpendicular to the closure element. The guide rail is mounted rotatably on each of the levers via a respective bearing, wherein said bearing likewise has a rotation axis perpendicular to the closure element.

In addition to the insulating function already described above, the closure device according to the invention has the advantage that it can be opened both manually and also in an automated manner if a movable structural part is provided which can exert a horizontal force on the guide rail at the time when access to the interior of the container is required. This advantageous mode of operation is described in more detail below using the example of a reagent vessel container in an automatic analysis apparatus.

By actuating the guide rail, i.e. by exerting a horizontal force, the closure element, which is preferably plate-shaped, is displaced in one plane.

By arranging the guide rail on the levers which connect the closure element and the fastening element, it is possible to obtain the displacement of the closure element via a lever in the physical sense, i.e. to obtain an increase in the distance of displacement at the cost of greater application of force. It is thereby possible to achieve a more complete opening of the closure element and better accessibility to the interior of the container. The bearings for the rotatable bearing of the guide rail can be mounted at any point of the levers, as long as the point is at a sufficient distance from the fastening-element-side bearing of a lever. The bearings for the rotatable bearing of the guide rail can also be arranged on the levers in such a way that they have the same rotation axis as the closure-element-side bearings for the levers.

If the two fastening-element-side bearings and the two closure-element-side bearings of the two mutually parallel levers are understood as the corner points of a parallelogram, the displacement of the closure element then corresponds to a change of the angles of the parallelogram.

In a preferred embodiment, the closed position, in which the closure element covers the opening of the container lid, corresponds to a position in which the internal angles of the parallelogram measure 90 degrees. In such a position, the maximum spacing of the closure element from the fastening element is achieved. In turn, the distance of displacement is maximized in this way, with the described advantages.

In another advantageous embodiment, the side of the parallelogram that connects the closure-element-side bearings to each other has a greater length than one of the other sides. With such dimensions, the levers can pivot to such an extent that, in an open position in which the closure element does not cover the opening of the container lid, the levers lie in a line, i.e. all the bearings are arranged in a line. This permits still further opening of the lid plate and in turn maximizes the distance of displacement, with the advantages described above.

The guide rail is preferably arranged parallel to an imaginary connecting line between the closure-element-side bearings.

Moreover, the guide rail preferably has, along the longitudinal axis thereof, a first portion curving in the direction of the fastening element, and a second, rectilinear portion. This has the advantage that, when access to the interior of the container is desired, any movable structural part (for example a portion of a device for moving reagent vessels into and out of a reagent vessel container) can be brought toward the curving end of the guide rail and can apply a horizontal force to the guide rail. If the structural part is moved parallel to the guide rail, the closure element is pushed aside by the curving shape of the end. When the structural part reaches the rectilinear portion of the guide rail, the closure element remains in the open position.

Advantageously, the curving portion of the guide rail is wave-shaped, i.e. without edges, but with a constantly changing curvature. If a movable structural part is guided along the guide rail, the wave shape of the curving portion of the guide rail reduces friction, and possible jamming is avoided. The automatic closure system is therefore less susceptible to failure.

In another advantageous embodiment, the closure device according to the invention comprises at least one restoring element, which is assigned to at least one of the bearings of the two levers or to the guide rail and has the effect that the closure element is moved from the open position to the closed position.

The restoring element is preferably a spring element, for example in the form of a leg spring, tension spring or compression spring. Suitable in particular is a leg spring of which the first leg is connected to the fastening element, and of which the second leg is connected to one of the levers.

The restoring element preferably acts to restore a position in which the internal angles of the above-described parallelogram measure 90 degrees.

In another embodiment of the closure device according to the invention, the closed position, in which the closure element covers the opening of the container lid, is assigned a limit stop, and the restoring element exerts a force in the direction of the limit stop.

A further subject of the present invention concerns a container lid with at least one opening, in which an above-described closure device is arranged on the opening. The closure device is connected to the container lid via the fastening element. The connection can be releasable or non-releasable. A releasable connection can be a screwed connection, for example. A non-releasable connection can be a weld, an adhesive bond or a rivet connection, for example.

In a particular embodiment of the container lid, the edge of the opening of the container lid is inclined, and the closure element has a wedge shape corresponding to this edge incline. This has the advantage that the closure element, when it is moved horizontally from the closed position to the open position, slides away from the opening without any appreciable friction. At the same time, in the closed position, a contact pressure is obtained, such that the opening is tightly closed.

A further subject of the present invention concerns a reagent vessel container for an automatic analysis apparatus, comprising a container lid as described above. The container lid can be connected to the reagent vessel container or simply placed with a form fit thereon. A connection can be produced, for example, via a hinge or a thread.

The reagent vessel container preferably has a plurality of receiving positions for reagent vessels, and a transport system for moving the receiving positions with the reagent vessels. The transport system can be of a linear configuration, or it can be a transport system that rotates about a perpendicular axis, e.g. a rotatable wheel or a rotatable disk.

A particular embodiment of the reagent vessel container comprises a rotatable wheel with receiving positions for reagent vessels, wherein the opening of the container lid extends in the radial direction starting from the center point of the rotatable wheel. In reagent vessel containers of this kind with concentrically arranged circles of receiving positions for reagent vessels, the access to a specific reagent container is made possible by rotating the rotatable wheel and positioning a desired reagent container under the opening in the container lid.

Preferably, the opening in the container lid of the reagent vessel container is designed such that reagent vessels can be inserted into the reagent vessel container, and can be removed from the reagent vessel container, through the opening. Alternatively, the opening in the container lid is designed such that a pipetting device has access to a reagent vessel through the opening.

A preferred reagent vessel container comprises a cooling unit for cooling the interior of the container, for example a Peltier element.

A further subject of the present invention concerns an automatic analysis apparatus with a reagent vessel container according to the invention and with a device for insertion and removal of reagent vessels into and out of the reagent vessel container, wherein said device has a mechanism for receiving a reagent vessel, preferably a gripper. The device for insertion and removal of reagent vessels preferably comprises a transfer arm, which is movable parallel to the guide rail of the closure device according to the invention and which can exert a horizontal force on the guide rail. This has the particular advantage that the closure device fastened to the lid of the reagent vessel container can be actuated automatically at the moment when the device for insertion and for removal of reagent vessels approaches the reagent vessel container in order to perform a reagent vessel transfer.

In an advantageous embodiment, the transfer arm, on which the gripper is secured, has a contact element, preferably a roller, which engages in the guide rail of the closure device on the container lid. This reduces the friction on the guide rail and reduces the susceptibility to failure. In addition, the lower degree of friction means that a lower degree of material wear can be expected, which extends the lifetime of the system.

The advantages achieved by the invention are in particular that, as a result of the mechanical actuation of the closure device by means of a guide rail on a self-restoring closure element that is displaceable in parallel, it is possible to achieve a particularly simple sealing as required of a reagent vessel container in an automatic analysis apparatus. The described closure mechanism reliably seals the reagent vessel container during phases when no access is needed, and it thereby reduces the amount of heat that enters.

Figure 2:
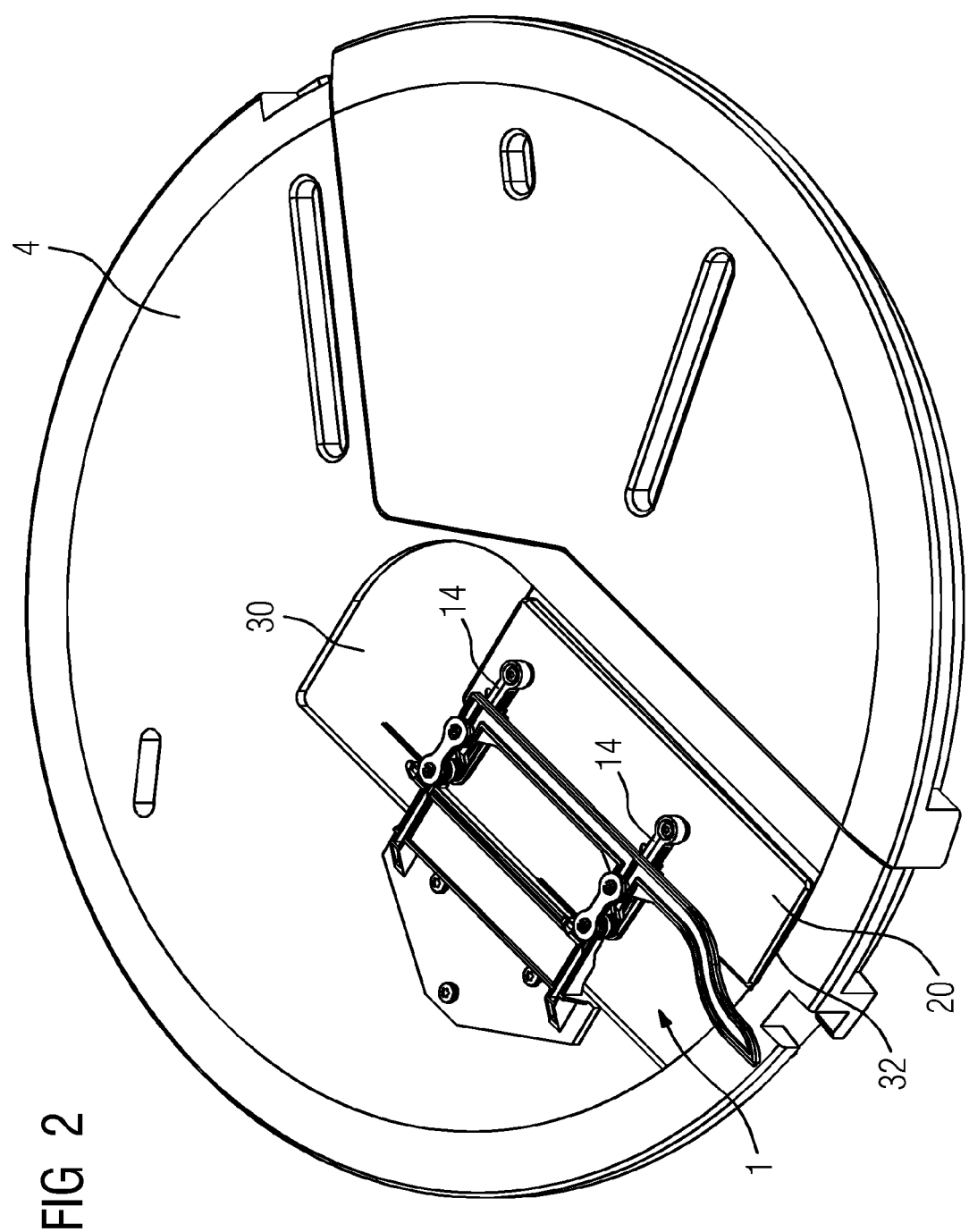
Figure 3:
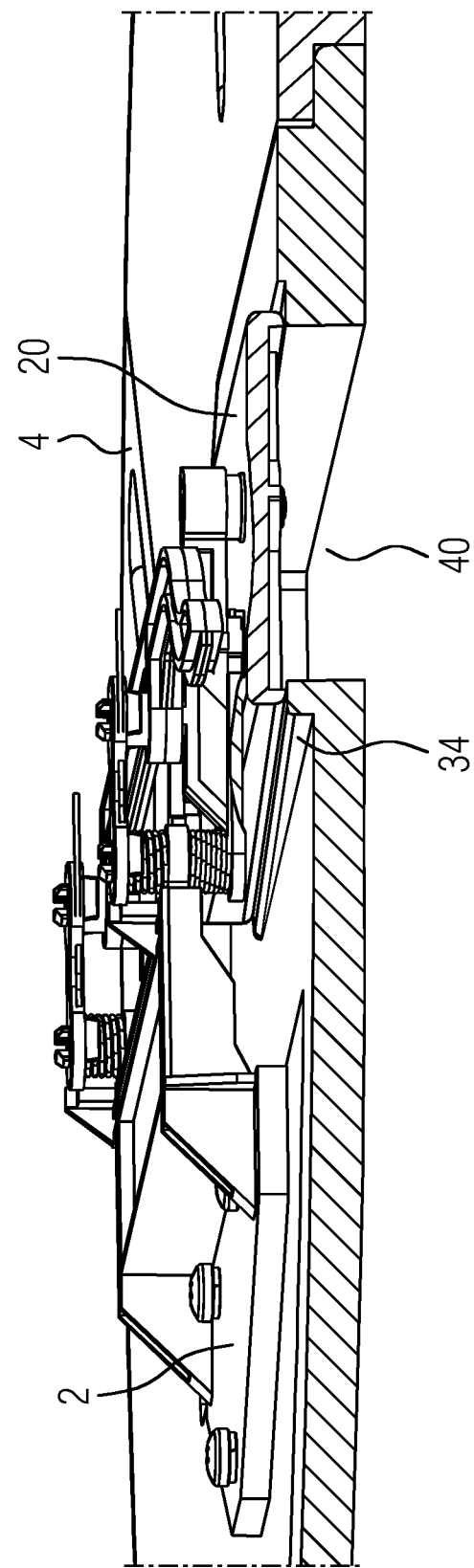
Figure 4:
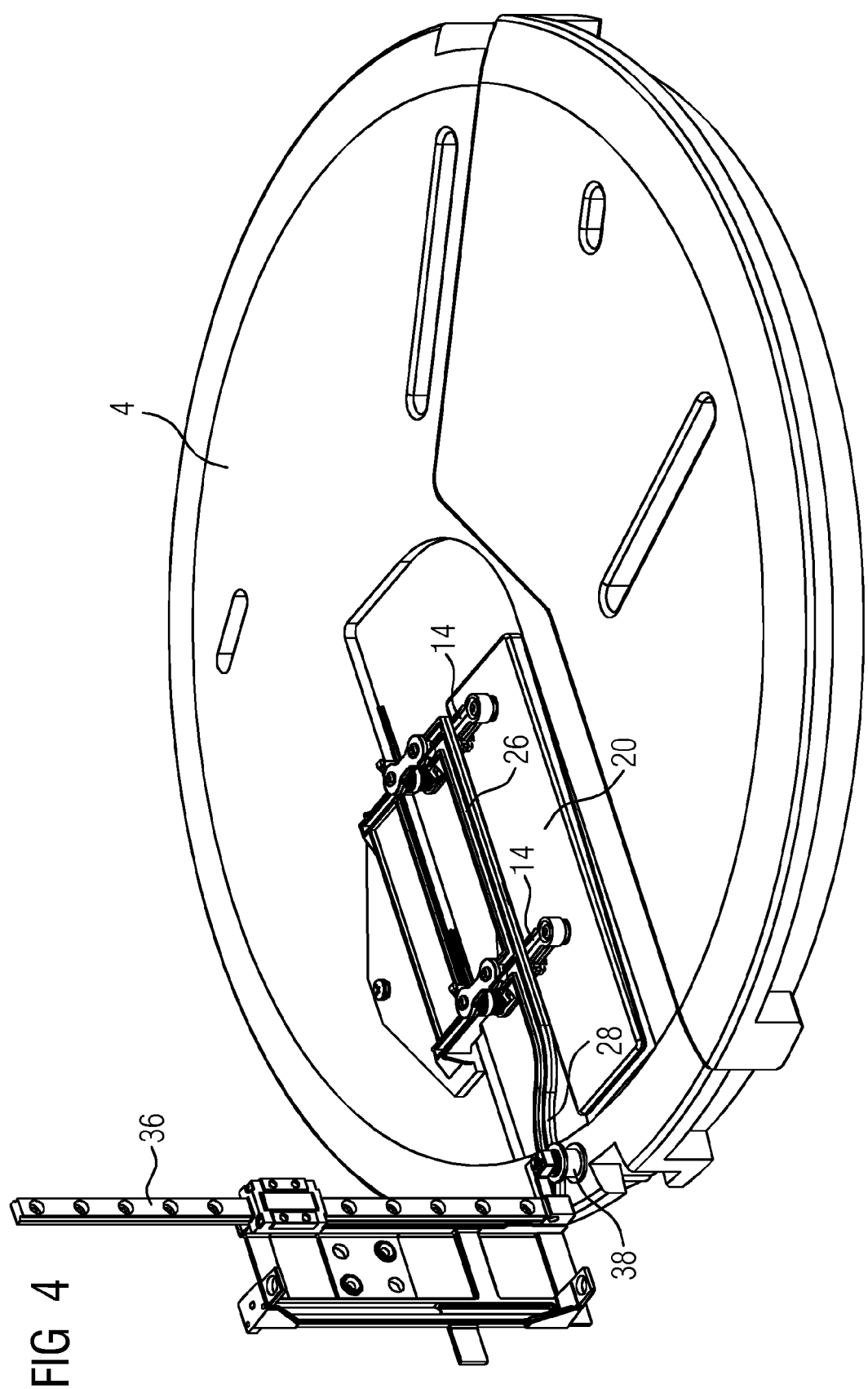
Figure 5:
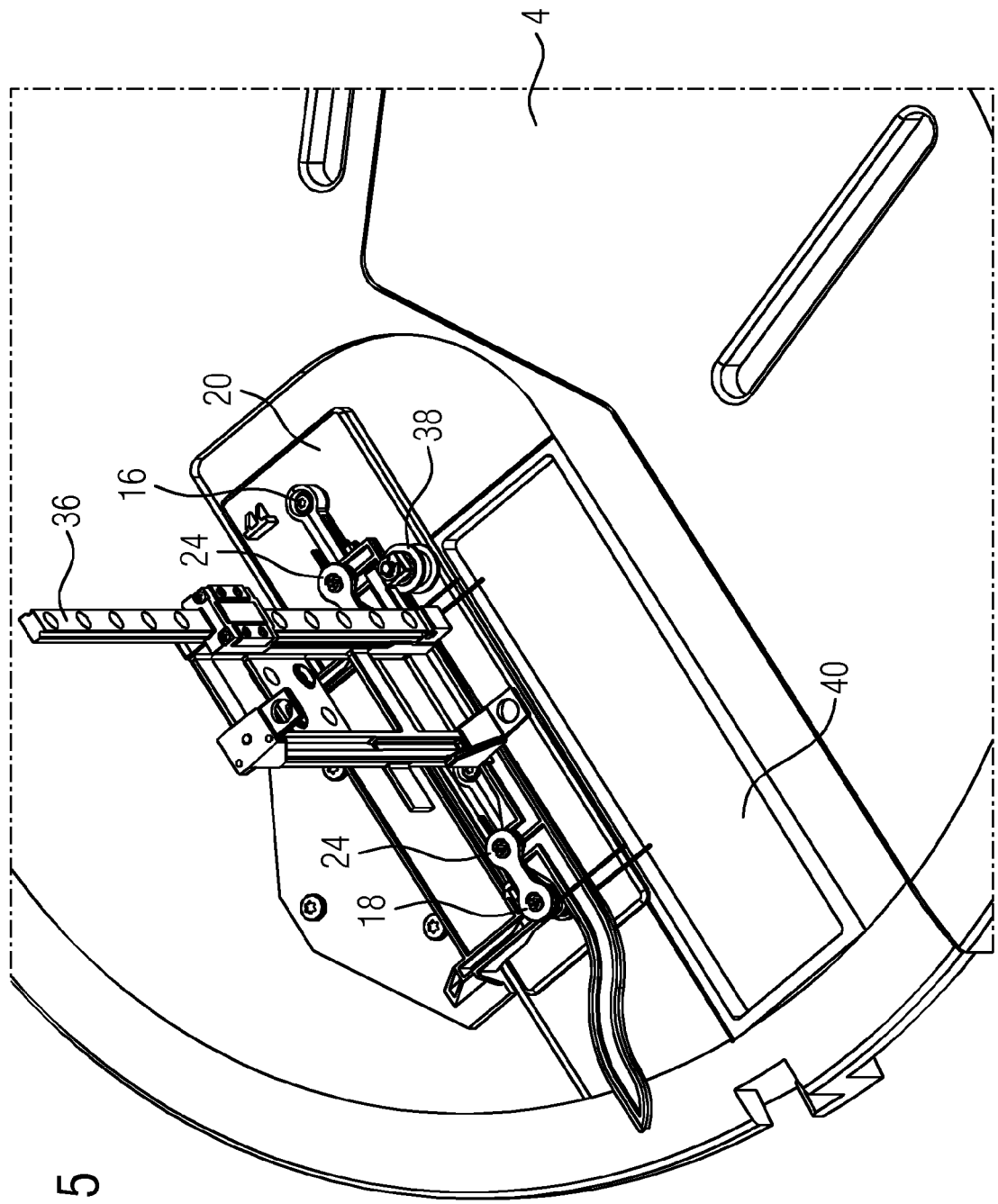
Figure 6:
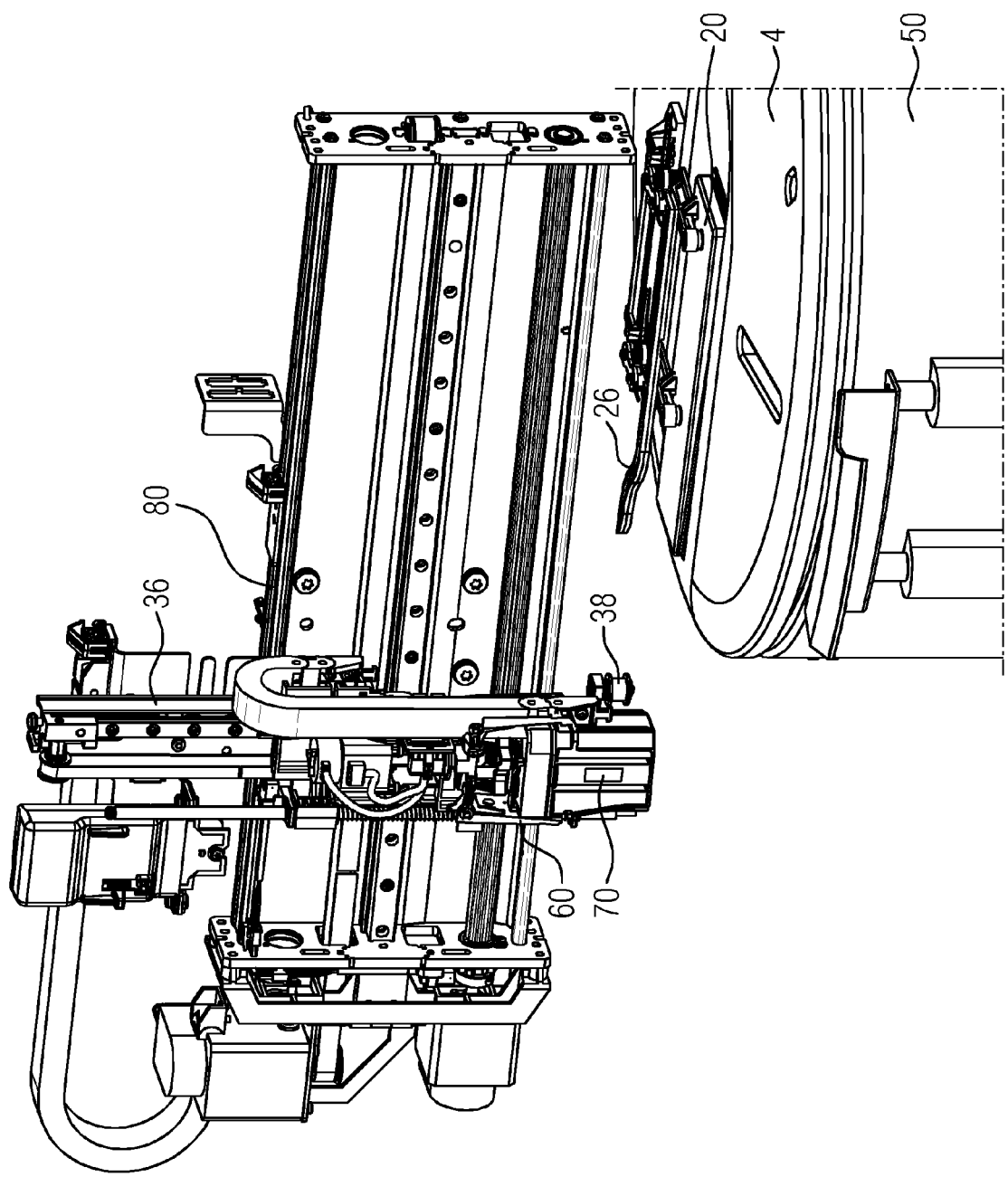

An illustrative embodiment of the invention is explained in detail with reference to a drawing, in which:

FIG. 1 shows a closure device according to the invention,

FIG. 2 shows the closure device in the closed position, arranged on the opening of a container lid, FIG. 3 shows a cross-sectional drawing of the closure device in the closed position, arranged on the opening of a container lid, FIG. 4 shows a closure device in the closed position, having a transfer arm with a gripper device, FIG. 5 shows a closure device in the open position, having a transfer arm with a gripper device, and FIG. 6 shows a detail of an automatic analysis apparatus with a reagent vessel container, and with a device for insertion and removal of reagent vessels.

Identical parts are provided with the same reference signs in all of the figures.

FIG. 1 shows a closure device 1 suitable for closing an opening in a container lid. The closure device 1 firstly comprises a fastening element 2 for mounting on a container lid, for example on a lid of a reagent vessel container (see FIG. 2). For this purpose, the fastening element 2 has mounting holes 6. The fastening element 2 comprises a base plate 8, and a plate 10 which is elevated in a plane parallel to the base plate 8 and protrudes above the base plate 8. The plate 10 is substantially rectangular and has, at the ends of its distal edge as seen from the base plate 8, two fastening-element-side bearings 18 which are designed as slide bearings and of which the axes are oriented perpendicularly with respect to the surface of the plate 10.

Two identical levers 14 are mounted in the bearings 18 respectively via an axial pin, which levers 14 are substantially rod-shaped and have, at their ends, closure-element-side bearings 16 which are likewise designed as slide bearings and of which the axes are oriented in parallel. The closure-element-side bearings are arranged on a rectangular closure element 20 of wedge-shaped profile. The bearings 18, 16 form a rectangle and are therefore displaceable in the manner of a parallelogram.

Each of the fastening-element-side bearings 18 fastened to the fastening element 2 is assigned a respective leg spring 22, of which the legs are assigned to the fastening element 2 and to the levers 14. The force of the leg springs 22 acts toward the right as seen from the fastening element 2.

Approximately one third of the way along each of the levers 14 as seen from the fastening element 2, further pins are arranged which are oriented parallel to the other bearing axes. Bearings 24, again designed as slide bearings, are arranged on the pins. These bearings 24 are fastened to a guide rail 26 arranged spaced apart in the direction of the closure element 20. The guide rail 26 is oriented parallel to a line connecting the closure-element-side bearings 16.

The guide rail 26 extends rectilinearly between the bearings 24. It is continued in the direction of the spring force and has a curving portion 28, which is wave-shaped. The portion 28 initially curves by about thirty degrees in the direction of the fastening element 2, then curves back to form a saddle, which curve back is oriented almost parallel to the rectilinear area of the guide rail 26, and it then bends again to a point in the direction of the fastening element 2.

FIG. 2 is a plan view of a circular lid 4, which is suitable for covering a reagent vessel container, with a closure device 1. In the reagent container (not shown), a plurality of concentric circles of receiving positions for reagent vessels are arranged on a rotatable wheel. The reagent vessels are accessed via a gripper or a pipetting device. The container lid 4 has a rectangular opening concealed by the closure element 20 in FIG. 2. The opening extends radially from the center point of the lid 4, and the closure device 1 is arranged correspondingly. Access to each receiving position is therefore ensured since, by rotation of the wheel below the lid 4 and by radial movement of the gripper or of the pipetting device over the opening, each point on the wheel can be reached.

The opening is let into a depression 30, of which the length corresponds to the sum of the side lengths of the closure element 20, and of which the width corresponds to twice the width of the closure element 20. The closure element 20 is moved inside the depression 30. The size of the depression 30 means that the levers 14 can be rotated by a maximum of ninety degrees. In the closed position shown in FIG. 2, the restoring force of the springs is limited by a limit stop 32, which is formed from an edge of the depression 30. Arranged about the circumference of the opening is a seal, which is designed rising toward the limit stop 32 and is thus shaped matching the wedge shape of the closure element 20. By means of the wedge shape together with the shape of the seal, a contact pressure is obtained in the closed state and, therefore, a tight closure.

FIG. 3 shows, in a cross-sectional drawing, the arrangement from FIG. 2, the closure device 1 in the closed position and arranged on the opening 40 of a container lid 4. FIG. 3 shows more clearly the opening 40 with the seal 34, and the wedge shape of the closure element 20 in the closed state.

FIGS. 4 to 6 show a movable transfer arm 36, on which can be secured a gripper for the transfer of reagent containers or a pipetting device. The transfer arm 36 is movable in the radial direction with respect to the wheel with the reagent vessel containers. A movement perpendicular to this direction is suppressed by a guide (not shown in detail). The transfer arm 36 is controlled in an automated manner by the control unit (not shown) of the automatic analysis apparatus.

A roller 38, secured on the transfer arm 36, is arranged at the height of the guide rail 26 and engages in the latter on the closure element side. In the rest position of the transfer arm 36 as shown in FIG. 4, the roller 38 is arranged at the end of the curving portion 28 of the guide rail 26.

When access to the reagent vessel container is enabled by the control unit, the transport arm 36 travels in the direction of the center point of the wheel. By means of the curving shape of the portion 28, a force acts on the guide rail 26 in the direction of the fastening element 2. This force causes a movement of the closure element 20. The size of the individual structural parts is chosen such that the levers 14 have completed a movement about ninety degrees when the roller 38 has reached the rectilinear part of the guide rail 26. The bearings 16, 18, 24 then all lie on a line, and the closure device 1 is situated in a fully open position, as shown in FIG. 5.

As the transfer arm 36 moves farther, starting from the point shown in FIG. 5, a force acts only via the guide rail 26 in the direction of the fastening element 2. The closure element 20 is held in the open position. When the transfer arm 36 is moved back again, the restoring force of the leg springs 22 has the effect that the closure element 20 is brought automatically again to the closed position.

FIG. 6 shows a detail from an automatic analysis apparatus with a reagent vessel container 50 and with a device 80 for inserting and removing reagent vessels into and out of the reagent vessel container, wherein said device has a gripper 60 for receiving a reagent vessel 70. The gripper 60 is secured on a transfer arm 36, on which the roller 38 is also secured. When the transfer arm 36 charged with a reagent vessel 70 is moved toward the reagent vessel container 50, the roller 38 along with the reagent vessel 70 reaches the area of the container lid 4 that has the opening 40 through which reagent vessels 70 are to be inserted into the reagent vessel container 50 and are to be removed from the reagent vessel container 50. By engagement of the roller 38 in the guide rail 26, the closure element is brought to the open position at the moment when the gripper 60 reaches the opening 40.

The invention claimed is:

1. A device for closing an opening in a container lid, said device comprising:
    a fastening element for fastening the device on the container lid,
    a closure element, which is connected movably to the fastening element and which, in a closed position, covers the opening of the container lid and, in an open position, does not cover the opening of the container lid,
    a guide rail, which is connected movably to the fastening element and to the closure element and on which a horizontal force can act, as a result of which the closure element is movable from the closed position to the open position,
    wherein the fastening element and the closure element are connected by a pair of mutually parallel levers, which are each mounted rotatably in a fastening-element-side bearing and in a closure-element-side bearing, wherein the bearings have a rotation axis perpendicular to a top surface of the closure element, and
    wherein the guide rail is mounted rotatably on each of the levers via a respective bearing, and wherein each bearing has a rotation axis perpendicular to the top surface of the closure element.

2. The device as claimed in claim 1, wherein the guide rail is arranged parallel to an imaginary line between the closure-element-side bearings.

3. The device as claimed in claim 1, wherein the guide rail has, along the longitudinal axis thereof, a first portion curving in the direction of the fastening element, and a second, rectilinear portion.

4. The device as claimed in claim 1, further comprising at least one restoring element, which is assigned to at least one of the bearings and has the effect that the closure element is moved from the open position to the closed position.

5. The device as claimed in claim 4, in which the closed position is assigned a limit stop, the restoring element exerts a force in the direction of the limit stop, and a curving portion is arranged on that side of the guide rail in the direction of which the force acts.

6. The device as claimed in claim 4, in which the restoring element is a spring element of which a first leg is connected to the fastening element and a second leg is connected to one of the levers.

7. The device as claimed in claim 6, wherein the spring element comprises a leg spring, tension spring, or compression spring.

8. The device as claimed in claim 1, in which a curving portion of the guide rail is wave-shaped.

9. A container lid with at least one opening, wherein the container lid comprises the device claimed in claim 1 arranged on the at least one opening.

10. The container lid as claimed in claim 9, wherein the edge of the at least one opening is inclined, and the closure element has a wedge shape corresponding to the edge incline.

11. A reagent vessel container for an automatic analysis apparatus, comprising a container lid as claimed in claim 9.

12. The reagent vessel container as claimed in claim 11, further comprising a rotating wheel with receiving positions for reagent vessels, wherein the at least one opening of the container lid extends in the radial direction starting from the center point of the rotating wheel.

13. The reagent vessel container as claimed in claim 11, wherein the at least one opening in the container lid is designed such that reagent vessels can be inserted into the reagent vessel container, and can be removed from the reagent vessel container, through the at least one opening.

14. The reagent vessel container as claimed in claim 11, wherein the at least one opening in the container lid is designed such that a pipetting device has access to a reagent vessel through the at least one opening.

15. An automatic analysis apparatus with a reagent vessel container as claimed in claim 11, and with a device for insertion and removal of reagent vessels into and out of the reagent vessel container, wherein said device has a mechanism for receiving a reagent vessel.

16. The automatic analysis apparatus as claimed in claim 15, wherein the mechanism for receiving a reagent vessel comprises a gripper.

17. The automatic analysis apparatus as claimed in claim 15, wherein the device for insertion and removal of reagent vessels comprises a transfer arm, which is movable parallel to the guide rail and which can exert a horizontal force on the guide rail.

18. The automatic analysis apparatus as claimed in claim 17, wherein the transfer arm has a contact element, which engages in the guide rail.

19. The automatic analysis apparatus as claimed in claim 18, wherein the contact element comprises a roller that engages in the guide rail.

* * * * *